(12) United States Patent
Seiger et al.

(10) Patent No.: US 12,004,913 B1
(45) Date of Patent: Jun. 11, 2024

(54) METHODS OF REPROCESSING A SURGICAL INSTRUMENT

(71) Applicant: STRYKER SUSTAINABILITY SOLUTIONS, INC., Tempe, AZ (US)

(72) Inventors: Jason Seiger, Gilbert, AZ (US); Brooke McDonald, Phoenix, AZ (US); Nicholas Ferentheil, Gilbert, AZ (US); Nathan Butters, Phoenix, AZ (US); Charles A. Forker, Lakeland, FL (US); Sachin Jain, Gurgaon (IN)

(73) Assignee: STRYKER SUSTAINABILITY SOLUTIONS, INC., Tempe, AZ (US)

( * ) Notice: Subject to any disclaimer, the term of this patent is extended or adjusted under 35 U.S.C. 154(b) by 378 days.

(21) Appl. No.: 17/328,402

(22) Filed: May 24, 2021

(51) Int. Cl.
*A61B 17/32* (2006.01)
*A61B 90/70* (2016.01)
*B08B 9/032* (2006.01)

(52) U.S. Cl.
CPC .............. *A61B 90/70* (2016.02); *A61B 17/32* (2013.01); *B08B 9/032* (2013.01); *A61B 2017/320032* (2013.01); *A61B 2217/005* (2013.01); *B08B 2209/032* (2013.01)

(58) Field of Classification Search
None
See application file for complete search history.

(56) References Cited

U.S. PATENT DOCUMENTS

| | | | |
|---|---|---|---|
| 9,095,366 B2 | 8/2015 | Sullivan et al. | |
| 9,155,454 B2 | 10/2015 | Sahney et al. | |
| 10,507,035 B2 | 12/2019 | Boudreaux et al. | |
| 2006/0216547 A1* | 9/2006 | Vance | F23R 3/007 428/697 |
| 2015/0209080 A1* | 7/2015 | Sullivan | A61B 17/32053 606/119 |
| 2016/0217542 A1* | 7/2016 | Coleman | G06Q 90/00 |
| 2019/0321094 A1* | 10/2019 | Stamm | B23P 6/00 |
| 2019/0321930 A1* | 10/2019 | Twomey | A61B 90/70 |
| 2020/0305998 A1* | 10/2020 | Kivioja | A61L 29/08 |
| 2020/0324028 A1* | 10/2020 | Zollinger | A61M 1/79 |
| 2022/0233118 A1* | 7/2022 | Cowe | A61B 5/150114 |

OTHER PUBLICATIONS

Cardiovascular Systems, Inc., "Diamondback 360 Peripheral Orbital Atherectomy System Webpage", https://csi360.com/diamondback-peripheral-orbital-atherectomy-system/, 2017-Present, 9 pages.

* cited by examiner

*Primary Examiner* — Kyle A Cook
(74) *Attorney, Agent, or Firm* — Howard & Howard Attorneys PLLC

(57) ABSTRACT

A method of reprocessing a surgical instrument that includes a handpiece having opposed shells secured together with a fastener, a shroud secured to the handpiece and overlaying the fastener and a portion of the handpiece, an outer shaft extending from the shroud and defining a cutting window, and a cutting shaft movable within the outer shaft and including a cutting tip for resecting tissue within the cutting window is disclosed. The method includes mutilating the shroud so as to remove the shroud from the handpiece, removing the fastener, separating the opposed shells to access an interior of the handpiece, servicing or replacing at least one component within the interior of the handpiece, securing the opposed shells to one another with the fastener or another fastener, and securing a replacement shroud to the handpiece.

17 Claims, 9 Drawing Sheets

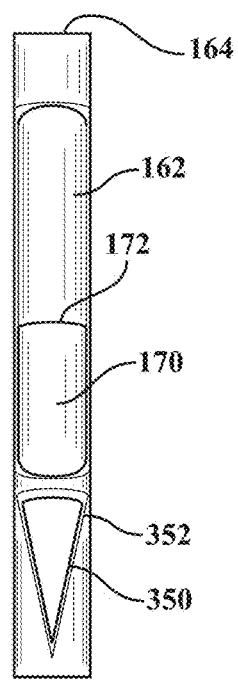
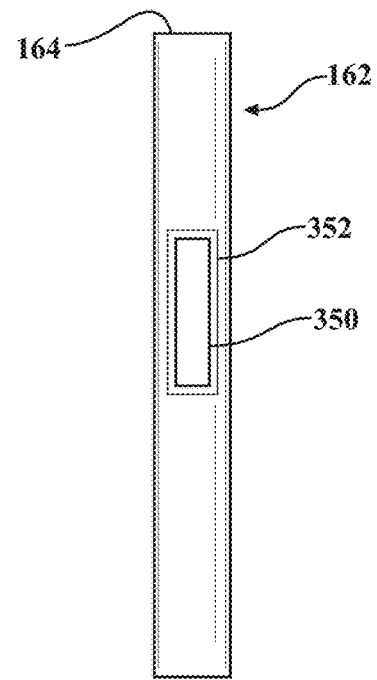
FIG. 7A  FIG. 7B
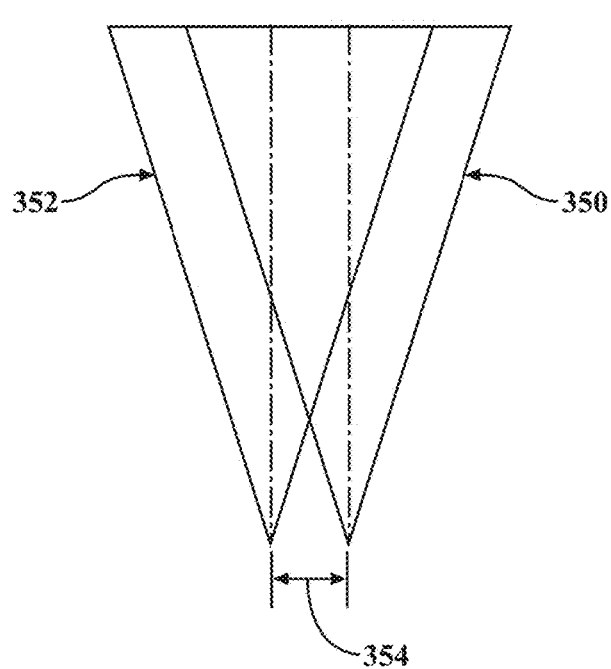
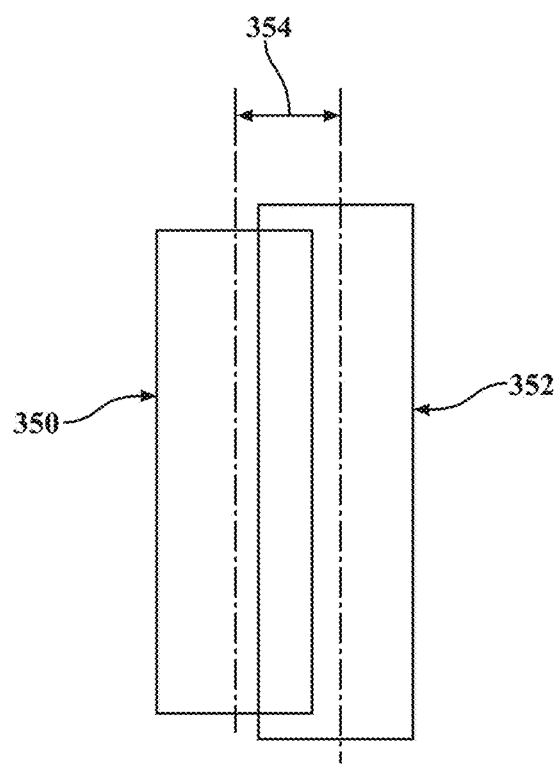
FIG. 7C  FIG. 7D

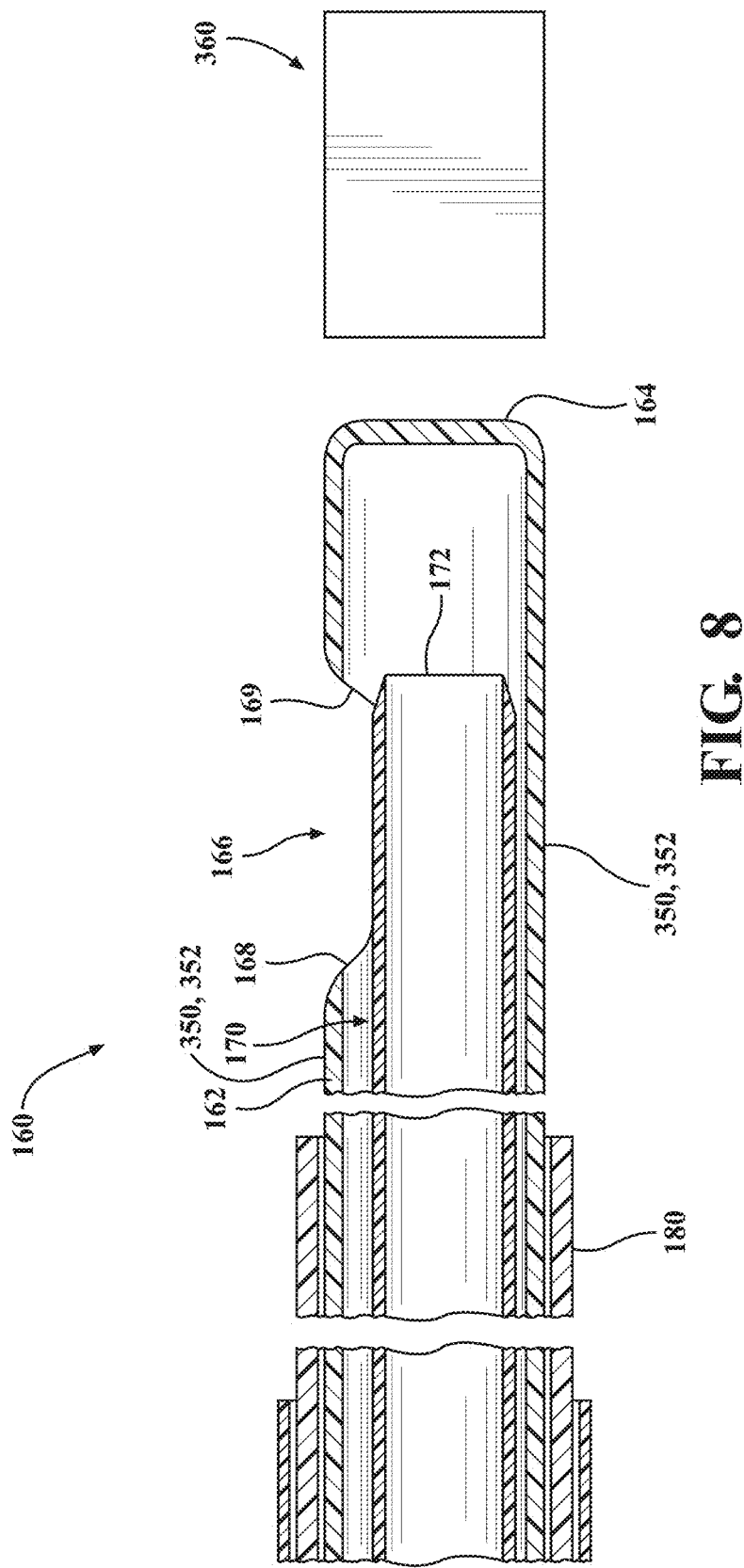

METHODS OF REPROCESSING A SURGICAL INSTRUMENT

BACKGROUND

Surgical instruments are often single-use and disposable, which leads to a significant amount of environmental waste. Further, certain components of the surgical instruments may be manufactured from materials that are not environmentally considerate, for example, polyvinylchloride. Users of the single-use surgical instruments are typically required to purchase a new instrument after each procedure, which is associated with increased cost. Standards for sterility and performance for surgical instruments generally are often exacting, and therefore past efforts to adequately reprocess surgical instruments are lacking. Therefore, there is a need in the art for improved methods for reprocessing surgical instruments to overcome one or more of the aforementioned shortcomings.

SUMMARY

A method of reprocessing a surgical instrument is provided. The instrument to be reprocessed includes a handpiece having opposed shells secured together with at least one fastener, and a shroud secured to the handpiece. The shroud overlays the fastener and a portion of the handpiece. Additionally, the instrument includes an outer shaft extending from the shroud and defining a cutting window, and a cutting shaft movable within the outer shaft and including a cutting tip for resecting tissue within the cutting window. The reprocessing method may begin by mutilating the shroud so as to remove the shroud from the handpiece. The fastener(s) are exposed. The shroud may be milled along with a portion of the handpiece to create a milled surface upon which the replacement shroud may be secured. Before or after the step of milling the shroud, the fastener is removed to allow the opposed shells to be separated. The opposed shells are separated in order to access an interior of the handpiece, and to service or replace at least one component within the interior of the handpiece. Certain cleaning steps to be described may be performed. The opposed shells are secured to one another with the fastener or another fastener and a replacement shroud is secured to the handpiece.

In order to mutilate the shroud, the instrument may first be secured to a fixture prior to milling. While the instrument is secured by the fixture, the shroud may be milled along with the portion of the handpiece. If desired, adhesive may be applied to the milled surface before securing the replacement shroud to the handpiece.

The method of reprocessing the surgical instrument may further include steps relating to the cutting shaft, the cutting tip, and the outer shaft. For example, the cutting tip may be severed from the cutting shaft before securing a replacement cutting tip to the cutting shaft. Alternatively, the cutting tip may be sharpened after the cutting shaft is removed from within the outer shaft. In another example, at least one of the outer shaft and the cutting shaft may be chemically or electrically treated. The outer shaft and cutting shaft may also be straightened.

The instrument being reprocessed according to the present methods may further include a section tubing assembly. In this case, the step of servicing or replacing at least one component may include cleaning a suction tubing assembly with a replacement suction tubing assembly. In order to clean the suction tubing assembly, the suction tubing assembly is decoupled from the handpiece, flushed with an aqueous solution, and recoupled to the handpiece. Alternatively, the suction tubing assembly may be decoupled from the handpiece, and an unused suction tube assembly may be coupled to the handpiece. Further, if the instrument includes a flexible drive cable, the method may include replacing the flexible drive cable with a replacement flexible drive cable.

In some embodiments, the surgical instrument may include original indicia disposed on the outer shaft that indicate the orientation of the instrument. If the instrument includes original indicia, the method may include marking the outer shaft with updated indicia. Further, the updated indicia may be at least partially disposed over the original indicia in order to avoid confusion by a user when attempting to determine the orientation of the instrument. Additionally, the updated indicia may be offset from the original indicia by a distance no greater than a predetermined threshold. If the updated indicia were offset from the original indicia by a distance above the predetermined threshold, a user may struggle to determine the orientation of the instrument.

In another embodiment, the instrument to be reprocessed includes a handpiece having opposed shells secured together with a fastener, and a shroud secured to the handpiece. Again, the shroud overlays the fastener and a portion of the handpiece. The method includes mutilating the shroud so as to remove the shroud from the portions of the opposed shells, and securing a replacement shroud to the portions of the opposed shells. Additionally, the shroud may be formed from a first material and the replacement shroud may be formed from a second material different than the first material. In an effort to make the instrument more environmentally sustainable, the second material may be a bio-based polymer that is more environmentally sustainable than the first material.

The step of mutilating the shroud may further include securing the surgical instrument to a fixture, milling the shroud, milling the portion of the handpiece to provide a milled surface, and securing the replacement shroud to the milled surface. When the shroud in mutilated according to the above method, the instrument may be secured to a fixture before proceeding with the method. The shroud may be milled along with a portion of the handpiece with the handpiece secured to the fixture. Milling the shroud and the handpiece creates a milled surface upon which the replacement shroud may be secured.

In certain embodiments, a reprocessing method may be applied to a surgical instrument that includes a handpiece and a shroud secured to the handpiece. Similar to the above two methods, this third method may also include securing the surgical instrument to a fixture so that the shroud may be milled and removed from the handpiece. Along with the shroud, the handpiece may be milled to provide a milled surface upon which a replacement shroud may be secured. Additionally, the method may also include applying an adhesive to the milled surface to secure the replacement shroud to the handpiece. The replacement shroud may be formed with a bio-based polymer that is more environmentally sustainable than material forming the shroud.

In another embodiment, a method of reprocessing a surgical instrument is provided. The instrument to be reprocessed includes a handpiece having opposed shells secured together with a fastener, and a shroud secured to the handpiece. The shroud overlays the fastener and a portion of the handpiece. Additionally, the instrument includes an outer shaft extending from the shroud and defining a cutting window, and a cutting shaft movable within the outer shaft and including a cutting tip for resecting tissue within the cutting window. Further, a memory module is attached to the instrument, for example, disposed within the handpiece. The memory module has instrument management data stored therein. The method includes mutilating the shroud so as to remove the shroud from the handpiece and securing a replacement shroud to the handpiece. The memory module may be removed, and a replacement memory module is attached to the outer shaft.

In another embodiment, a method of reprocessing a surgical instrument is provided. The surgical instrument includes a handpiece, a shroud secured to the handpiece, and an outer shaft extending from the shroud. Additionally, a memory module is provided on the instrument management data stored therein. The method includes mutilating the shroud so as to remove the shroud from the handpiece and securing a replacement shroud to the handpiece. The instrument management data stored on the memory module is replaced such that the instrument management data indicates that the surgical instrument is a new surgical instrument.

In another embodiment, a method of reprocessing a surgical instrument is provided. The instrument to be reprocessed includes a handpiece having opposed shells secured together with a fastener, and a shroud secured to the handpiece. The shroud overlays the fastener and a portion of the handpiece. Additionally, the instrument includes an outer shaft extending from the shroud and defining a cutting window, and a cutting shaft movable within the outer shaft and including a cutting tip for resecting tissue within the cutting window. Further, a memory module is attached to the outer shaft and has instrument management data stored therein. The method includes mutilating the shroud so as to remove the shroud from the handpiece and securing a replacement shroud to the handpiece. The instrument management data stored on the memory module is replaced such that the instrument management data indicates that the surgical instrument is a new surgical instrument.

The instrument management data may include at least one of use data and authentication data. More specifically, the use data may include at least one of a number of times the surgical instrument has been used, the amount of time that the surgical instrument has been used, and a time stamp indicating when the surgical instrument was created. Further, the authentication data may include at least one of a unique identifier and an encrypted identifier.

In another embodiment, a method of reprocessing a surgical instrument is provided. The instrument to be reprocessed includes a handpiece having opposed shells secured together with a fastener, and a shroud secured to the handpiece. The shroud overlays the fastener and a portion of the handpiece. Additionally, the instrument includes an outer shaft extending from the shroud and defining a cutting window, and a cutting shaft movable within the outer shaft and including a cutting tip for resecting tissue within the cutting window. Further, a memory module is attached to the outer shaft and has instrument management data stored therein. The instrument management data includes at least one of use data and authentication data. More specifically, the use data comprises at least one of a number of times the surgical instrument has been used, the amount of time that the surgical instrument has been used, and a time stamp indicating when the surgical instrument was created. The authentication data includes at least one of a unique identifier and an encrypted identifier. In such an embodiment, the instrument communicates with a surgical generator comprising a drive assembly configured to selectively actuate the cutting shaft and a control module configured to communicate with the memory module. During this communication, the control module is further configured to determine if the instrument management data indicates that the cutting shaft of the surgical instrument may be actuated by the surgical generator. The drive assembly actuates the cutting shaft if the control module determines that the surgical instrument is a new surgical instrument.

In order to evaluate the status of the surgical instrument, the control module may further include a database having a list of maximum use values stored therein. The list of maximum use values includes at least one of a maximum number of uses, a maximum time of use, and a maximum age. Once the control module receives the use data from the memory module, it compares the received use data against the list of maximum use values stored on the database, and determines that the surgical instrument is a new surgical instrument if the received use data is not above at least one of the maximum number of uses, the maximum time of use, and the maximum age of the surgical instrument.

If the instrument management data includes the time stamp, the control module may determine that the surgical instrument is above the maximum age by receiving the use data comprising the time stamp and comparing said use data against a present time indicator.

If the instrument management data includes authentication data, the control module may further include a database having a list of valid unique identifiers stored therein. In this case, the control module is further configured to receive the authentication data from the memory module and compare the received authentication data against the list of valid unique identifiers stored on the database. After this comparison, the control module determines that the surgical instrument is a new surgical instrument if the received authentication data corresponds to a valid unique identifier stored within the list of valid unique identifiers. Alternatively, the database may include a list of prohibited unique identifiers stored therein. Similar to the previous determination, the control module may determine that the surgical instrument is not a new surgical instrument if the received authentication data corresponds to a prohibited unique identifier stored within the list of prohibited unique identifiers.

In another embodiment, a method of reprocessing a surgical instrument is provided. The instrument to be reprocessed includes a handpiece having opposed shells secured together with a fastener, and a shroud secured to the handpiece. The shroud overlays the fastener and a portion of the handpiece. Additionally, the instrument includes an outer shaft extending from the shroud and defining a cutting window, and a cutting shaft movable within the outer shaft and including a cutting tip for resecting tissue within the cutting window. Further, a memory module is attached to the outer shaft and has instrument management data stored therein. In such an embodiment, the instrument communicates with a surgical generator which includes a drive assembly configured to selectively actuate the cutting shaft and a control module configured to receive the instrument management data from the memory module. The method includes mutilating the shroud so as to remove the shroud from the handpiece and securing a replacement shroud to the handpiece. Once the shroud has been replaced, the instrument management data stored on the memory module may be replaced such that the instrument management data indicates that the surgical instrument is a new surgical instrument Additionally, the instrument management data may include at least one of use data and authentication data. If so, the use data includes at least one of a number of times the surgical instrument has been used, the amount of time that the surgical instrument has been used, and a time stamp indicating when the surgical instrument was created. Further, the authentication data includes at least one of a unique identifier and an encrypted identifier. The control module may receive the instrument management data and compare it against a database stored on the control module. After receiving the data, the control module determines that the surgical instrument is a new surgical instrument by comparing the received instrument management data from the memory module against at least one of a maximum use value, a list of unique identifiers, and a list of encrypted identifiers stored in the database.

During reprocessing, the step of replacing the instrument management data stored on the memory module may take many forms. For example, the number of times the surgical instrument has been used, or the amount of time that the surgical instrument has been used, may be set to a value below the maximum use value stored in the database. In a like manner, the time stamp that indicates when the surgical instrument was created may be set to a value that indicates that the surgical instrument was created at the time that the surgical instrument was reprocessed. Authentication data may also be altered. For example, the unique identifier may be set to a value that matches a corresponding value contained within the list of unique identifiers stored in the database. If the instrument management data includes the encrypted identifier, the encrypted identifier may be set to a value that matches a corresponding value contained within the list of encrypted identifiers stored in the database.

BRIEF DESCRIPTION OF THE DRAWINGS

FIGS. 7A-7B show a set of indicia on the outer shaft of the tissue removal device of FIG. 1.

FIGS. 7C-7D show an offset between indicia on the outer shaft of the tissue removal device of FIG. 1.

FIG. 8 shows a distal end of the tissue removal device of FIG. 1 along with a sharpening assembly.

DETAILED DESCRIPTION

Figure 1:
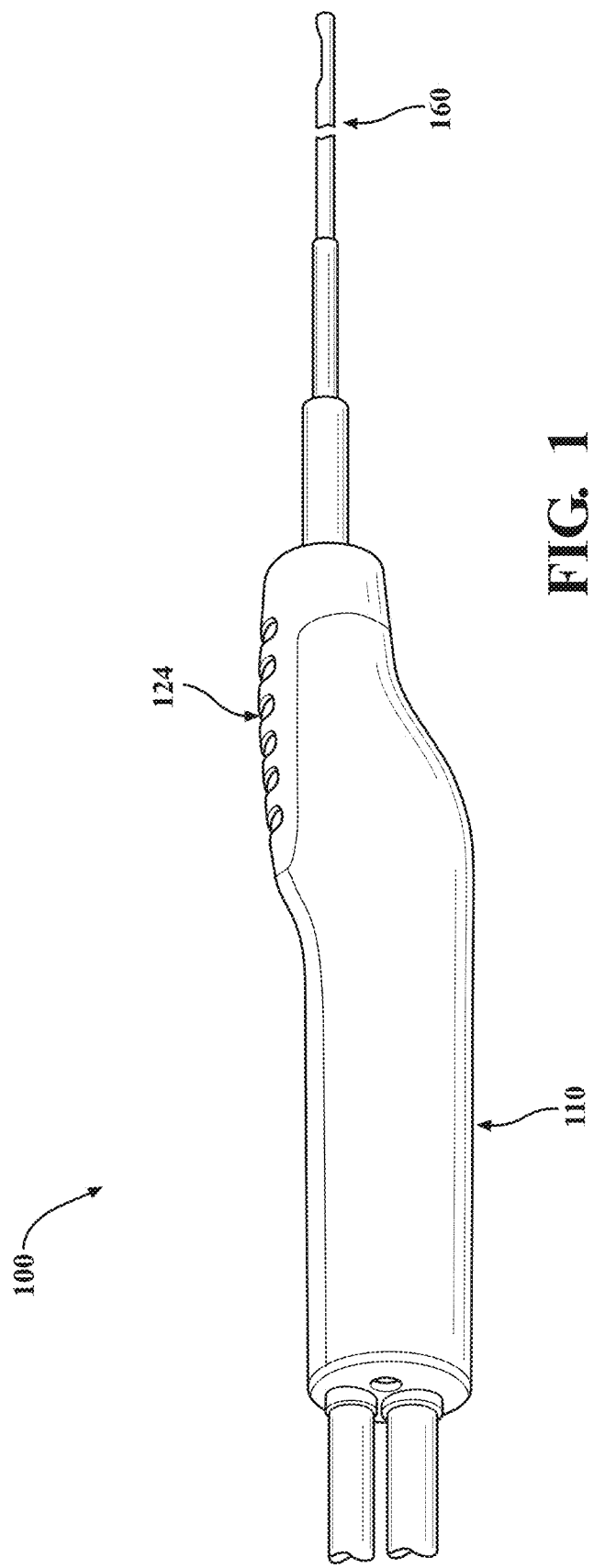
FIG. 1 is a perspective view of a tissue removal device to be reprocessed according to the teachings of the present disclosure.

Referring now to the drawings, a method for reprocessing a surgical instrument is provided. In particular, the reprocessing method may be suitable for use with a broad selection of instruments, henceforth referred to as an instrument 100, such as a tissue resection device. Other examples of the instrument 100 may comprise a tissue morcellator for resecting polyps and fibroids. Other like instruments are also contemplated, for example, the MyoSure tissue removal device, sold by Hologic and described by U.S. Pat. No. 9,095,366, the entire disclosure of which, except for any definitions, disclaimers, disavowals, and inconsistencies, is incorporated by reference herein.

Figures 2, 2A:
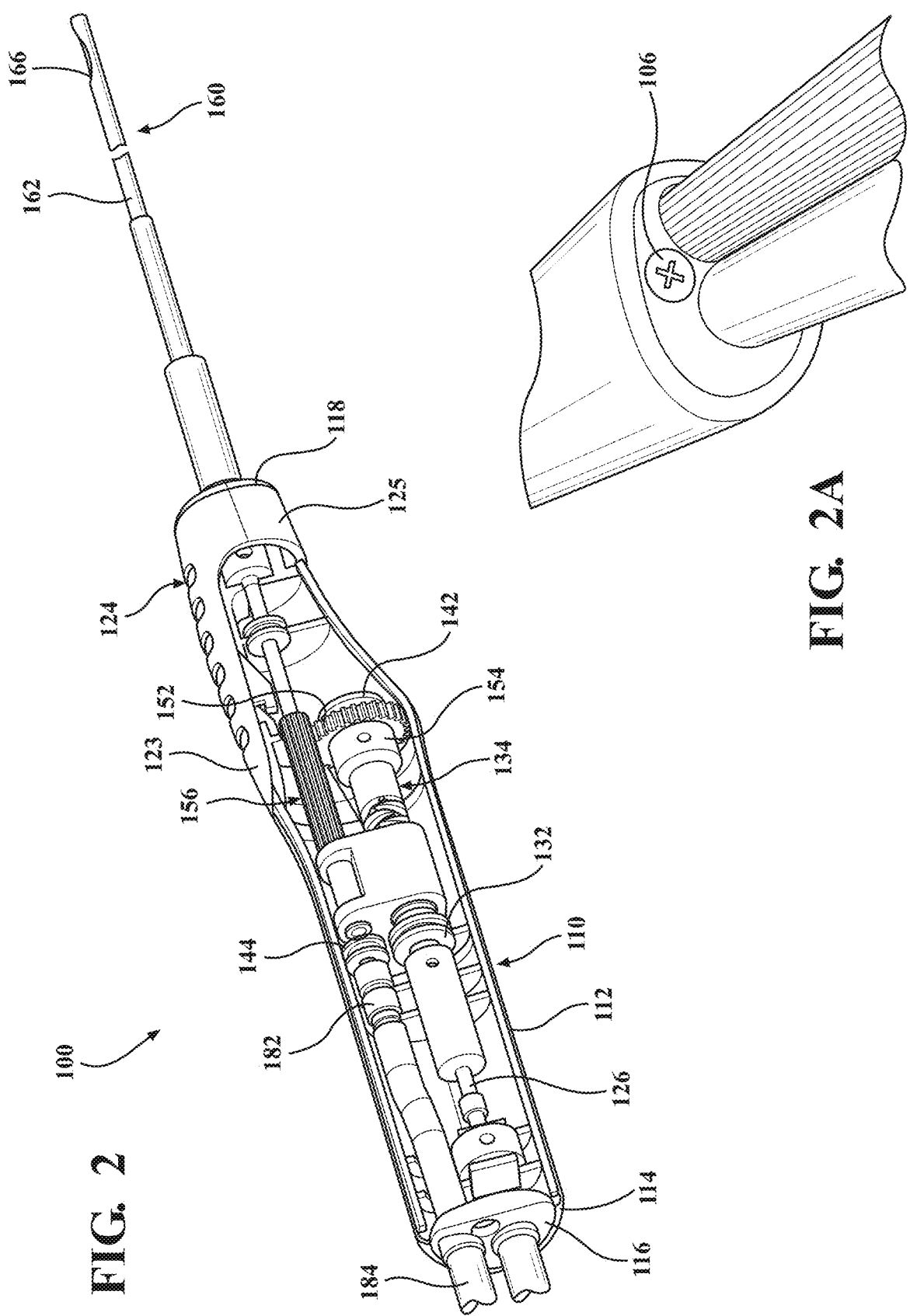
FIG. 2 is a perspective view of the tissue removal device of FIG. 1 with one of the opposing shells of the handpiece removed.
FIG. 2A shows a proximal end of the tissue removal device of FIG. 1.
Figure 3:
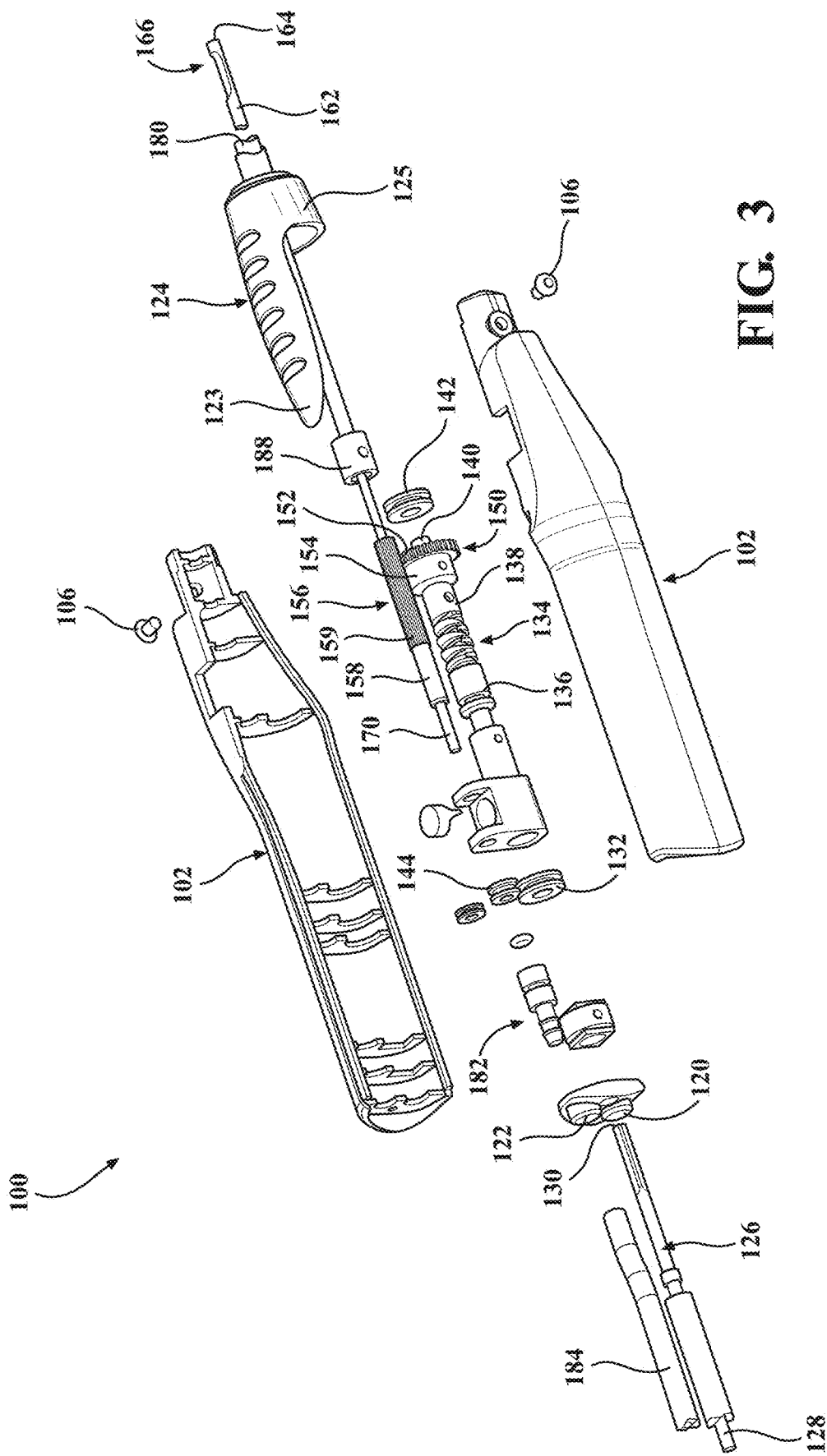
FIG. 3 is an exploded perspective view of the tissue removal device of FIG. 1.

Referring now to FIGS. 1 through 3, the tissue removal instrument 100 is shown in greater detail. The instrument 100 may comprise complementary opposing shells 102, each of which may be made of a rigid polymer or other suitable material. The opposing shells 102 may be joined together by fasteners 106, for example, by screws, to form an elongated hollow handpiece 110 comprising a side wall 112, an open proximal end 114, and an open distal end 118. The handpiece 110 may be bent or otherwise ergonomically shaped to fit comfortably in the hand of a user. A proximal cap 116 may be mounted in the proximal end 114, with the proximal cap 116 being shaped to include a first lumen 120 and a second lumen 122. The first lumen 120 may be used to receive, for example, a drive cable 126, and the second lumen 122 may be used to receive, for example, a suction tube 184. A shroud 124 may be mounted on the distal end of the instrument 100, and the shroud may include a longitudinal face 123 and a tubular end 125. The shroud 124 may be shaped to include a lumen through the tubular end 125, which may be used to receive, for example, a pair of coaxial cutting tubes.

The instrument 100 may further comprise the drive cable 126 adapted for rotation about its longitudinal axis. The drive cable 126, which may be an elongated unitary structure made of a suitably rigid metal or polymer, may be shaped to include a proximal end 128 and a distal end 130. The distal end 130 of the drive cable 126 may be inserted through a first annular bushing 132, and the first annular bushing 132 may be matingly mounted on a rib of the handpiece 110 via a circumferential slot provided in the bushing 132.

The instrument 100 may further comprise a translational drive shaft 134 adapted for rotation about its longitudinal axis. The translational drive shaft 134, which may be an elongated unitary structure made of a suitably rigid metal or polymer, includes a proximal end 136, an intermediate portion 138, and a distal end 140. The proximal end 136 of the translational drive shaft 134 may be coaxially mounted over and fixed to the distal end 130 of the drive cable 126. In this manner, the rotation of the translational drive shaft 134 may be mechanically coupled to the rotation of the drive cable 126. The intermediate portion 138 may be shaped to include a double helical portion comprising a right-handed threaded helical channel and a left-handed threaded helical channel. The distal end 140 of the translational drive shaft 134 may be appropriately dimensioned to be received within an opening in a second annular bushing 142, and the second annular bushing 142 may be matingly mounted on a rib of the handpiece 110 via a circumferential slot provided in the bushing 142.

The instrument 100 may further comprise a primary gear assembly 150 adapted for rotation. The primary gear assembly 150 is shaped to include a spur gear 152 and a tubular portion 154. The primary gear assembly 150 may be coaxially mounted over the intermediate portion 138 of the translational drive shaft 134 in an area between the double helical portion and the distal end 140, and the primary gear assembly 150 may be fixed to the translational drive shaft 134 using a pin inserted radially through the tubular portion 154 and into an opening provided in the translational drive shaft 134. In this manner, the rotation of the spur gear 152 may be mechanically coupled to the rotation of the translational drive shaft 134.

The instrument 100 may further comprise a secondary gear assembly 156 adapted for rotation about its longitudinal axis. The secondary gear assembly 156, which is an elongated, unitary, tubular structure made of a suitably rigid metal or polymer, is shaped to include a proximal portion 158 and a distal portion 159. The distal portion 159 may be in the form of an elongated spur gear. The distal portion 159 is engaged with the spur gear 152 of the primary gear assembly 150 so that the rotation of the spur gear 152 causes the rotation of the secondary gear assembly 156. The distal portion 159 of the secondary gear assembly 156 is elongated so that it may maintain engagement with the spur gear 152 even as the distal portion 159 of the secondary gear assembly 156 moves translationally relative to the spur gear 152.

The speed at which the distal portion 159 rotates (and, therefore, the speed at which the secondary gear assembly 156 rotates) may be the same as or different than the speed at which the spur gear 152 rotates, depending, for example, on the relative diameters of the two gears (the ratio of the rotational speeds of the two gears being inversely proportional to the ratio of the diameters of the two gears). Consequently, by appropriately dimensioning the spur gear 152 and the distal portion 159, one can achieve a desired rotational speed, even where the rotational speed of the external drive shaft is fixed. For example, in one embodiment, the distal portion 159 has a diameter that is one-fourth the diameter of the spur gear 152 and, therefore, rotates four times as fast as the spur gear 152. Therefore, if the external drive shaft has a speed of rotation of about 1500 rpm, the spur gear 152 would rotate at 1500 rpm and distal portion 159 of the secondary gear assembly 156 would rotate at 6000 rpm.

Referring to FIG. 8, the instrument 100 may further comprise a cutting mechanism 160. In the present embodiment, the cutting mechanism 160 may comprise an outer shaft 162 and an cutting shaft 170. The cutting shaft 170 may move rotationally and, at the same time, oscillate translationally relative to the outer shaft 162 in the manner to be described below. The outer shaft 162, which may be a unitary structure made of stainless steel or another similarly suitable material, includes an open proximal end, a closed distal end 164, and a lumen extending from the open proximal end to a point just prior to the closed distal end 164. The outer shaft 162 may be coaxially mounted within a strain relief member 180, with the proximal end of the outer shaft 162 disposed within the proximal end of the strain relief member 180. Further, the distal end 164 of the outer shaft 162 extends distally beyond the distal end of the strain relief member 180 for an extended distance, such as, for example, five inches. The proximal end of the outer shaft 162 may be fixed within a retainer 188.

The outer shaft 162 includes a cutting window 166 into which tissue may be captured and drawn, the cutting window 166 being located proximate to the distal end 164 of the outer shaft 162, such as, for example, 0.25 inches from the distal end. The cutting window 166 includes a proximal end 168 and a distal end 169. The proximal end 168 may slope gradually proximally, and distal end 169 may slope gradually distally. More specifically, the cutting window 166 may have a length of approximately 0.55 inches, the proximal end 168 may be a radial end having a radius of curvature of, for example, 0.085 inches, and the distal end 169 may be a radial end having a radius of curvature of, for example, 0.150 inches. The cutting window 166 may extend over a substantial portion of the circumference of the outer shaft 162, such as, for example, about 60% of the circumference.

The cutting shaft 170, which is an elongated unitary structure made of stainless steel or another similarly suitable material, includes a proximal end, a cutting tip 172, and a longitudinal lumen. The cutting tip 172 includes an external bevel, such as, for example, an external bevel of approximately 20 degrees. An intermediate length of the cutting shaft 170 may be coaxially received within the secondary gear assembly 156 and may be fixedly coupled to the secondary gear assembly 156 for translational and rotational movement therewith. The proximal end of the cutting shaft 170 may be slidably mounted within a suction tube connector 182, which may, in turn, be coupled to a suction tube 184 inserted through the lumen 122 of the proximal cap 116. An O-ring may be mounted within the suction tube connector 182 to maintain a good seal with the cutting shaft 170. A third annular bushing 144 mounted within the handpiece 110 may be used to receive the cutting shaft 170 and to maintain its alignment.

Figure 4:
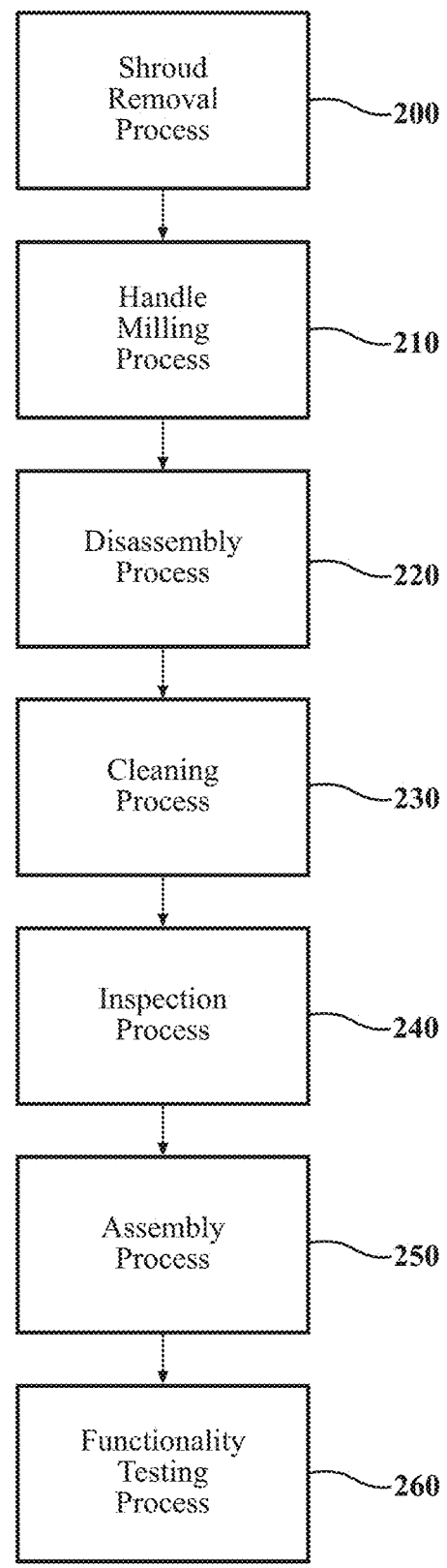
FIG. 4 is a flowchart illustrating a method of reprocessing the tissue removal device of FIG. 1.

Referring to FIG. 4, the present reprocessing method may begin with a shroud removal process 200. The shroud removal process 200 may start with a handle pre-wipe, during which any identifying markings are removed from the handpiece 110. The handle pre-wipe may also include corrosion treatment methods, which are used to remove corrosion from the metal components of the instrument 100. The shroud 124 may then be removed from the instrument 100 during the shroud removal process 200, either by mutilating the shroud 124 or by any other removal method.

In one embodiment, the instrument 100 may be placed in a shroud removal fixture during the shroud removal process 200. It is contemplated that the shroud removal fixture may be an automated machine that operates according to a set of instructions stored in non-volatile memory, such as read-only memory (ROM), or volatile memory, such as random access memory (RAM). The shroud removal fixture may secure the instrument 100 to prevent the instrument 100 from moving when the shroud 124 is mutilated during the shroud removal step 200. Once the instrument 100 is secured by the shroud removal fixture, the shroud removal fixture may then circumferentially grip the tubular end 125 of the shroud 124. After gripping the tubular end 125 of the shroud 124, the shroud removal fixture performs a twisting action to separate the shroud 124 from the handpiece 110. Such a twisting action may remove the tubular end 125 of the shroud 124, the longitudinal face 123 of the shroud 124, or both.

In some embodiments, the shroud 124 may be cut or grinded by hand in order to remove the shroud 124 from the handpiece 110. If the shroud 124 is removed by hand, the longitudinal face 123 of the shroud 124 may be grinded down or cut away from the handpiece 110. The tubular end 125 of the shroud 124 may also be grinded down or cut away from the handpiece 110.

In further embodiments, the instrument 100 may include a suction control mechanism (not pictured), such as a switch, integrated with the longitudinal face 123 of the shroud 124. If the instrument 100 being reprocessed includes the suction control mechanism, the reprocessing method may further include the removal of the mechanism during the shroud removal process 200.

Figure 5:
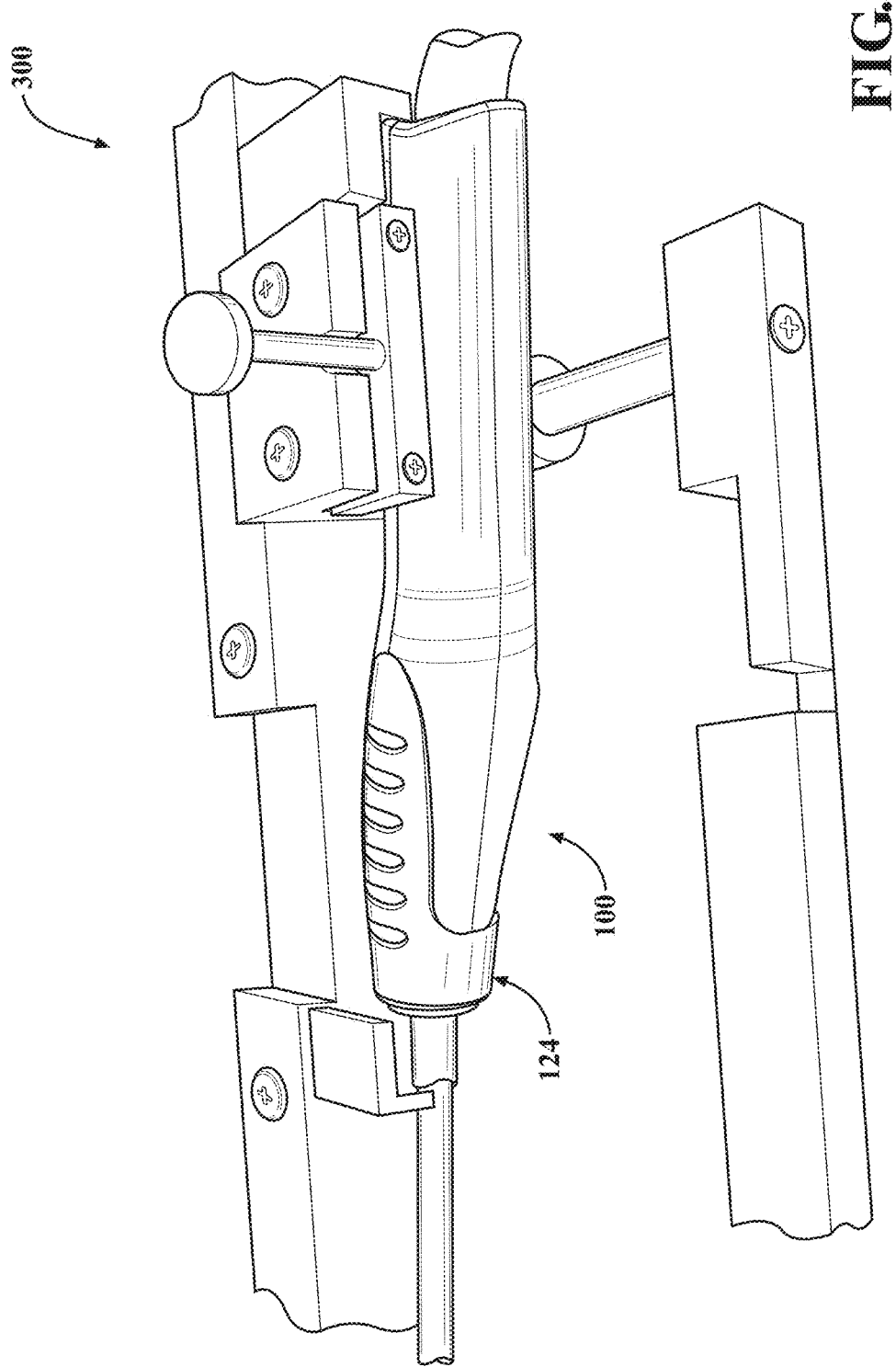
FIG. 5 shows the tissue removal device of FIG. 1 being restrained by a milling fixture.
Figure 6:
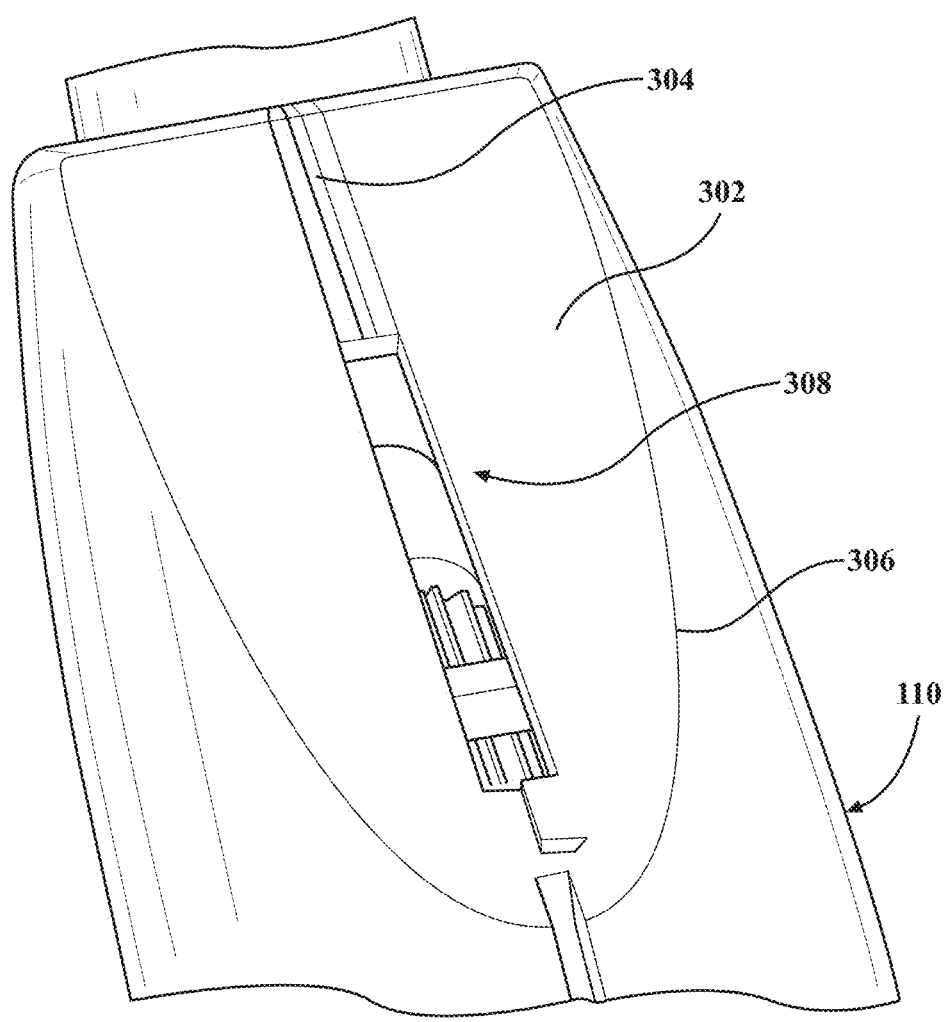
FIG. 6 shows a milled surface of a tissue removal device.

Referring to FIGS. 5 and 6, following the shroud removal process 200, the instrument 100 may be placed in a milling fixture 300 during a handle milling process 210 in order to create a milled surface 302 on the instrument 100. This process 210 removes any remainder of the shroud 124 still attached to the handpiece 110, any remaining adhesive, and may further remove a controlled amount of the underlying handpiece 110. This ensures a smooth and consistent milled surface 302 for applying a new shroud 124. It is contemplated that the replacement shroud 124 design may include additional material to compensate for the removed handpiece 110 material.

During the shroud removal process 200, the milled surface 302 may be created along, and centered on, a seam 304 where the opposing shells 102 join to form the handpiece 110. Additionally, the milled surface 302 may include an edge 306 that spans across a portion of the handpiece 110 and is centered on the seam 304. The edge 306 may be arcuate or rectangular in shape and is positioned at the border between the milled surface 302 and the rest of the handpiece 110. In some embodiments, the milled surface 302 may be deep enough into the handpiece 110 such that an elongated or circular slot 308 is formed in the handpiece 110. Each element 304, 306, 308 of the milled surface 302 may be considered when designing the replacement shroud 124, as this ensures that the replacement shroud 124 may be adequately secured to the milled surface 302 and handpiece 110 in general.

In some embodiments, the instrument 100 may be placed into the milling fixture 300 and the remainder of the shroud 124 may then be removed by computer numerical control (CNC) milling or another subtractive form of manufacturing. In one example, the remainder of the shroud 124 is removed, and the milled surface 302 is created, according to a computer-aided design (CAD) drawing or 3D model. In order to remove the remainder of the shroud 124, the longitudinal face 123 may be grinded down until the milled surface 302 is created. If the remainder of the shroud 124 is not removed by grinding the longitudinal face 123, the tubular end 125 may also be grinded down and removed from the handpiece 110.

After the handle milling process 210, the instrument 100 is disassembled according to a disassembly process 220. During this process 220, the fasteners 106 are removed and the handpiece 110 is separated into the pair of opposing shells 102. In certain embodiments, a number of additional fasteners, e.g. screws, may need to be removed before the handpiece 110 may be separated. Following the separation of the opposing shells 102, one or more of the following components are removed: the suction tube 184, the suction tube connector 182, the strain relief member 180, the outer shaft 162, the cutting shaft 170, the drive cable 126, and any or all bushings (for example, the first, second, and third annular bushings 132, 142, 144). If the instrument 100 includes a bleed tube, the bleed tube may also be removed. It is also contemplated that any other components may be removed if necessary for reprocessing. After the instrument 100 is disassembled according to the disassembly process 220, the removed components are flushed with an aqueous solution, labeled, and stored for future steps. Further, some of the components may be discarded during the disassembly process 220. If discarded, the component may be replaced by a substantially similar replacement component with certain replacement components being formed from materials that are more environmentally sustainable as to be described.

Still referring to FIG. 4, the disassembly process 220 is followed by a cleaning process 230. The cleaning process 230 may include at least one of cleaning the components surrounded by the handpiece 110 of the instrument 100, cleaning the outer shaft 162, cleaning the cutting shaft 170, cleaning the drive cable 126, and cleaning the suction tube 184. Any of the components may be cleaned with an aqueous solution and subsequently dried.

According to the present embodiment, the aqueous solution may include distilled water as well as other additives. For example, the aqueous solution may include a detergent, such as an enzymatic detergent, a pH-neutral detergent, or a high-pH detergent. Exemplary detergents include, but are not limited to, for example, Tergazyme® from Alconox, Inc and MediClean Forte from Chemische Fabrik Dr. Weigert GmbH & Co. The components of the instrument 100 may be soaked in the aqueous solution, scrubbed by a brush or other scrubbing tool, sprayed by the aqueous solution at a high pressure, and subjected to ultrasonic cleaning. If necessary, the instrument 100 and its components may be rinsed and dried during the cleaning process 230.

The instrument 100 may also be inspected according to an inspection process 240. The inspection process 240 may include confirming the state of the disassembled and cleaned components of the instrument 100. During this process 240, it may be determined that certain components need to be replaced rather than repurposed for future use. Replacement components are substantially similar to their respective original components but may be made of a more sustainable material, such a bio-plastic or bio-polymer.

Referring to FIGS. 4 and 7A-7D, the inspection process 240 may further include updating an original indicia 350 on the outer shaft 162. The original indicia 350 provides the operator with an indication of the orientation of the outer shaft 162, and the original indicia 350 may be shaped like an arrow, rectangle, or other suitable geometry. Additionally, the instrument 100 may include more than one original indicia 350.

In one embodiment, the instrument 100 includes at least two original indicia 350, with both of the indicia 350 located near the distal end of the outer shaft 162. For example, as shown in FIGS. 7A and 7B, an arrow may be positioned on the outer shaft 162 in line with the proximal end 168 of the cutting window 166 and a rectangle may be positioned on the outer shaft 162 radially opposite the cutting window 166. Including both the arrow and the rectangle as the original indicia 350 allows an operator to ascertain the orientation of the outer shaft 162 by looking at either indicia 350. Further, by placing the two indicia 350 on opposite sides of the outer shaft 162, the original indicia 350 can remain in view of the operator regardless of the instrument's 100 orientation about its longitudinal axis.

When the instrument 100 is reprocessed according to the present method, the original indicia 350 may be updated due to the possibility of its removal during the disassembly or cleaning process 220, 230. An updated indicia 352 may be marked onto the outer shaft 162 in a similar location to the original indicia 350, or even on top of the original indicia 350. For example, the updated indicia 352 may be laser etched onto the outer shaft 162. Since the updated indicia 352 is meant to replace the original indicia 350, the updated indicia 352 may be marked in a manner that results in an indicia offset 354 that is as small as possible.

Referring to FIGS. 7C and 7D, the indicia offset 354 is the distance between the longitudinal axis of the original indicia 350 and the longitudinal axis of the updated indicia 352. The indicia offset 354 may be measured according to the longitudinal axis, or midline, of any suitable geometry. As shown in FIG. 7C, if the original indicia 350 and the updated indicia 352 are both triangular, the indicia offset 354 may be measured from the midline of one rectangle to the midline of the other rectangle. Further, as shown in FIG. 7D, if the original indicia 350 and the updated indicia 352 are both rectangular, the indicia offset 354 may be measured from the midline of one rectangle to the midline of the other rectangle. The midline, as discussed here, is a line running from a proximal end of the indicia 350, 352 to the distal end of the indicia 350, 352, and located halfway along the radial width of the indicia 350, 352.

The original indicia may have been placed on the outer shaft 162 by the original manufacturer in an inconsistent manner, and the indicia offset 354 is preferred to be as small as possible. In the present embodiment, the indicia offset 354 is no greater than a predetermined threshold. The predetermined threshold of the indicia offset 354 is no greater than approximately 0.035 inches, and more particularly no greater than approximately 0.025 inches, and even more particularly no greater than 0.015 inches. If the instrument 100 includes multiple original indicia 350, then each of the multiple original indicia 350 may be replaced by updated indicia 352.

Referring to FIGS. 4 and 8, the inspection process 240 further includes a tip replacement, a sharpening of the cutting shaft 170, further straightening of the cutting shaft 170, or a combination therein. If it is desirable to replace the tip of the device, at least one of the distal ends of the cutting and outer shafts 170, 162 may be severed and replaced. For example, the cutting shaft 170 may be severed at a certain distance from the cutting tip 172 and a replacement piece that includes a new cutting tip 172 may be welded to the cutting shaft 170. When the cutting tip 172 is welded to the cutting shaft 170, an attachment location is established at a distance from the cutting tip 172 on the cutting shaft 170. For example, the attachment location may be 2 inches from the cutting tip 172. In order to make sure that the cutting tip 172 is severed in its entirety, the cutting tip 172 may be severed between the attachment location and the proximal end of the cutting shaft 170.

FIG. 8 includes a sharpening assembly 360 for sharpening the cutting shaft 170. It is contemplated that the cutting tip 172 may be sharpened either after removed from the outer shaft 162, or after removing the cutting shaft 170 from within the outer shaft 162. The cutting tip 172 may be sharpened by the sharpening assembly 360 while the sharpening assembly 360 is actuating, while the cutting shaft 170 is actuating, or a combination of the two. The cutting tip 172 may also be sharpened according to an electrosharpening chemical process.

Following the inspection process, an assembly process 250 begins with an incoming inspection of a set of replacement components, followed by a kitting of the instrument 100. Kitting is a process by which a number of related components are combined into a common item. In the present disclosure, the kitting involves combining the set of replacement components with a set of reprocessed components as detailed above. Since the kitting predominantly involves setting the components into either of the opposing shells 102 before combining these to form the handpiece 110, the term handpiece 110 is used when describing setting the components into either of the opposing shells 102. Additionally, although the kitting is described sequentially, the described steps can be performed in any order.

First, the retainer 188 may be attached to the cutting shaft 170, the outer shaft 162 may be attached to the cutting shaft via the retainer 188, the translational drive shaft 134 may be attached to the second annular bushing 142, and the cutting shaft may be attached to the third annular bushing 144. Concurrently or sequentially with the first set of kitting steps above, the suction tube 184 and the drive cable 126 are added into the handpiece 110. The suction tube 184 may be a replacement suction tube 184 made of a non-hazardous material such as polyurethane, or it may be the flushed suction tube 184. Additionally, the drive cable 126 may be a replacement drive cable 126 made of a corrosion resistant material (e.g., stainless steel), carbon steel material, or any other suitable material. The drive cable 126 may be inserted through the first lumen 120 of the proximal cap 116, while the suction tube 184 may be inserted through the second lumen 122 of the proximal cap 116. Once the suction tube 184 is through the second lumen 122, it can then be attached to the suction tube connector 182 to form an airtight connection. If the instrument 100 includes a suction bleed tube (not pictured), the suction bleed tube is also attached to the suction tube connector 182. If the instrument 100 includes a switch (not pictured) for turning the instrument 100 on and off, the switch may be attached to the handpiece 110. After the suction tube 184 is attached to the suction tube connector 182, the suction tube connector is set into the handpiece 110. Further, lubrication is applied to at least one of the cutting shaft 170, the translational drive shaft 134, outer shaft 162, or any other members that experience motion during use.

After kitting the components as described above, the mentioned components are set into the handpiece 110, but the opposing shells 102 of the handpiece 110 are not yet mated. Before mating the opposing shells 102, the reprocessed instrument 100 may be visibly inspected, either by an operator or by an automated computer system. This inspection allows an operator to confirm that all of the components were assembled correctly and that the instrument 100 may continue to be reprocessed.

During the assembly process 250, and after the visible inspection, the opposing shells 102 may be mated together and the fasteners 106 may be attached to the handpiece 110. To ensure a strong connection, adhesive may be applied to the fasteners 106. Once the handpiece 110 is reconstituted by the combined pair of opposing shells 102, adhesive is applied to the milled surface 302 and the replacement shroud 124 may be mated with the handpiece 110. Although adhesive is used to mate the replacement shroud 124 with the handpiece 110 in the present embodiment, it is also contemplated that other methods could be used. For example, the replacement shroud 124 may use mechanical features, such as ribs or screws, to mate with the handpiece 110. Alternatively, the replacement shroud 124 may be laser or ultrasonically welded onto the handpiece 110. The replacement shroud 124 may be geometrically distinct from the original shroud 124 to compensate for the milled surface 302. Additionally, the replacement shroud 124 may be made of a bio-based plastic such as Tenite or another like material. The replacement shroud 124 may also be created using additive manufacturing.

The instrument 100 may also include a suction control mechanism (not pictured) integrated into the shroud 124. If the shroud 124 includes the suction control mechanism, the replacement shroud 124 may also include the suction control mechanism. During the assembly process 250, but before the shroud 124 is mated to the handpiece 110, the suction control mechanism may be attached to the suction tube 184 via the suction bleed tube.

The instrument 100 may also include a drive cable assembly (not pictured) removably attached to the instrument 100 that includes the drive cable 126. It is contemplated that the drive cable assembly could also be reprocessed according to the present method. If desired, the drive cable assembly may be detached from the instrument 100 during the disassembly process 220, cleaned during the cleaning process 230, inspected during the inspection process 240, and reattached to the instrument 100 during the assembly process 250.

After the instrument 100 has been assembled according to the assembly process, the instrument 100 is tested for functionality during a functionality testing process 260. The instrument 100 may be operated in a manner that confirms whether the reprocessing method was successful. Further, the device may be testing for leaks during this process 260. The instrument may include suction elements, such as the suction tube 184 and the suction bleed tube, and these elements may be prone to leaks if improperly reprocessed.

During the functionality testing process 260, a memory module 410 may be attached to the instrument 100. For example, the memory module 410 may be attached to at least one of the outer shaft 162 and the handpiece 110. Alternatively, if the instrument 100 being reprocessed already included the memory module 410, the memory module 410 may be altered or replaced. The memory module 410 may be at least one of a barcode, a radio frequency identification (RFID) tag, or any other device used to identify surgical instruments. The memory module 410 may also include non-volatile memory (NVM). The NVM may comprise other types of memory including, for example, programmable ROM (PROM), erasable programmable ROM (EPROM), electrically erasable programmable ROM (EEPROM), or battery backed random-access memory (RAM) such as dynamic RAM (DRAM), Double-Data-Rate DRAM (DDRAM), and/or synchronous DRAM (SDRAM).

Figure 9:
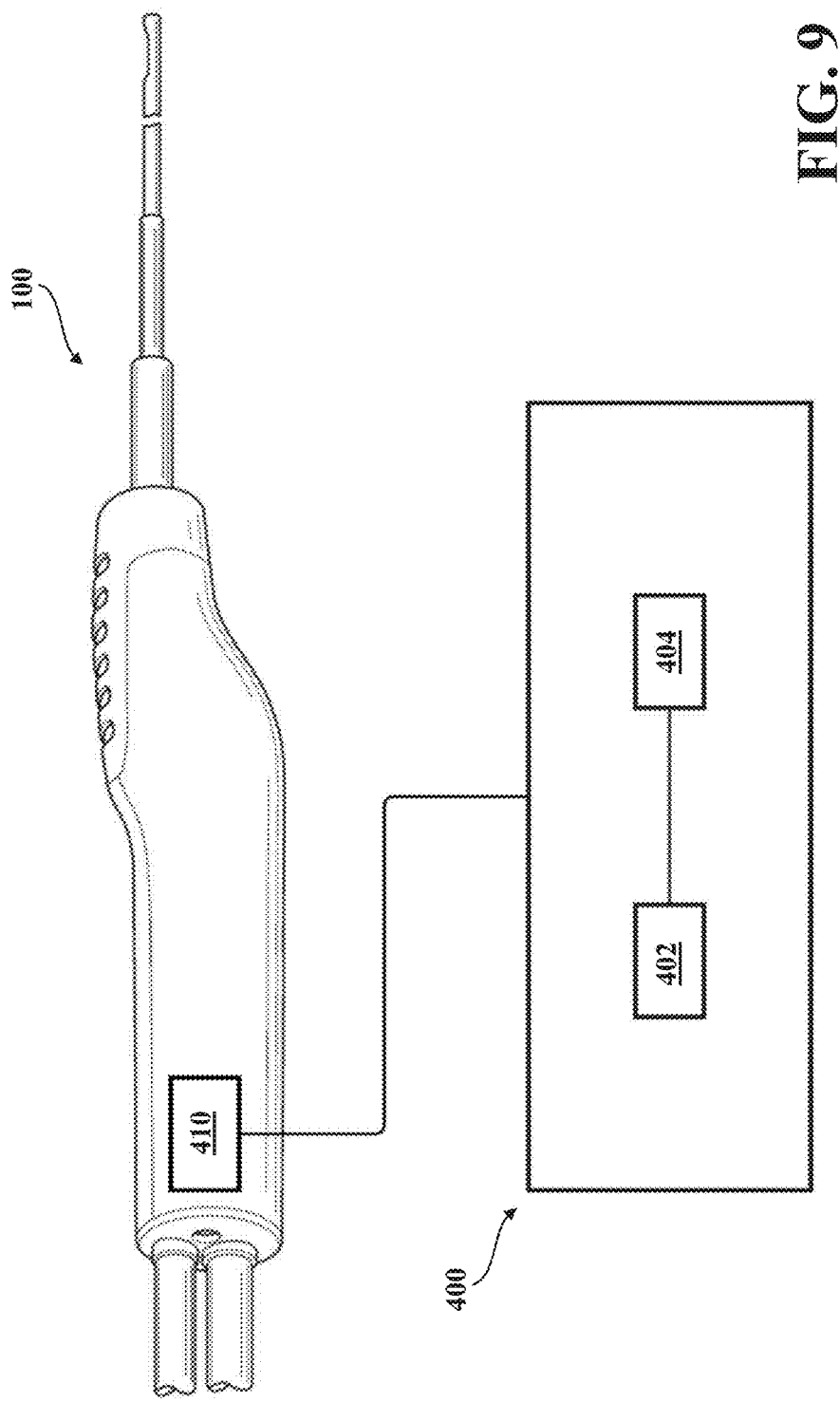
FIG. 9 shows the tissue removal device of FIG. 1 operatively connected to a surgical generator.

Referring to FIG. 9, the instrument 100 may be operatively connected to a generator 400 and the generator 400 may include a drive assembly 402. More specifically, the proximal end 128 of the drive cable 126 may be connected to the drive assembly 402. In such an embodiment, the drive assembly 402 and the cutting shaft 170 may be rotationally linked. Further, the generator 400 may include a control module 404 for communicating with the memory module 410 and, thus, the instrument 100. The control module 404 may include a database and may determine whether to enable actuation of the drive assembly 402 by communicating with the memory module 410. The memory module 410 may be configured to store instrument management data. For example, the memory device may store use data, authentication data, and other data that may be relevant for management of the instrument 100. Additionally, the database may be configured to store information utilized by the control module 404. During the reprocessing method described herein, the instrument management data may be altered in such a way that the instrument 100 is identified as a new instrument 100 by the generator 400 via the control module 404. This may be accomplished by writing new data to the memory module 410, deleting existing data from the memory module 410, or by replacing the memory module 410 with a replacement memory module 410.

In some embodiments, the generator 400 may be configured to selectively disable and enable features, such as actuation of the drive assembly 402, according to signals received by the control module 404 from the memory device attached to the instrument 100. In such an embodiment, the instrument 100 may be reprocessed according to a method that results in the memory device sending signals to the control module 404 that enable features of the generator 400.

The memory module 410 may store use data. For example, the use data may consist of at least one of a number of times the instrument 100 has been used, the amount of time that the instrument 100 has been used, and a time stamp indicating when the instrument 100 was created. In such an example, the control module 404 may read the use data from the memory device and determine whether the features of the generator 400 are available to the instrument 100. If the use data includes the number of times the instrument 100 has been used, or the amount of time that the instrument 100 has been used, the control module 404 may include a maximum value for such data. The generator 400 may disable select features if the memory device reports that the instrument 100 has been used more times than the maximum value or for a longer time than the maximum value. The time stamp, on the other hand, may be read by the control module 404 to determine whether the instrument 100 is too old. Such a determination is used to stop an operator from using the instrument 100 if there is a possibility that the instrument has deteriorated. The control module 404 may include a present time indicator for such a determination.

During the functionality testing process 260, the use data stored on the memory module 410 may be altered or reset. After the use data is altered or reset, the memory module 410 may contain use data that indicates to the control module 404 that the instrument 100 is a new device. One example is to set at least one of the number of times the instrument 100 has been used, and the amount of time that the instrument has been used, to a value that is below the maximum value. Another example is to set the time stamp to a time which indicates that the instrument 100 was created more recently. More specifically, the time stamp may be replaced with a date and time corresponding to the date and time that the instrument 100 was reprocessed according to the reprocessing method contained herein.

The memory module 410 may further store authentication data. For example, the authentication data may include a unique identifier (UID). In such an example, the control module 404 may read the UID from the memory device and evaluate the received UID against a database of valid, and invalid, UIDs stored on the control module 404. If the control module 404 determines that the received UID is valid, the control module 404 may allow the instrument 100 to utilize certain features of the generator 400. Alternatively, if the control module 404 determines that the received UID is invalid, the control module 404 may disable certain features of the generator 400. The control module 404 may utilize authentication data to prohibit unauthorized devices from being controlled by the generator 400.

In further embodiments, the memory module 410 may include other types of authentication data, such as an encrypted identifier. Such an embodiment may include back-and-forth communication, i.e. a handshake, between the memory module 410 and the control module 404. It is contemplated that the handshake may include at least one of symmetric encryption and asymmetric encryption to determine whether the instrument 100 is authenticated by the control module 404. Authentication, via symmetric and asymmetric encryption, may further include passwords, secret keys, public keys, private keys, and other elements used to accomplish encrypted communication. If the instrument 100 is authenticated by the control module 404, the control module 404 may enable certain features of the generator 400. Alternatively, if the control module 404 fails to authenticate the instrument 100, the control module 404 may disable certain features of the generator 400. Like the other embodiments that include other types of authentication data, this authentication process deters using the generator 400 to control unauthorized devices.

During the functionality testing process 260, the authentication data stored on the memory module 410 may be altered or reset. After the use data is altered or reset, the memory module 410 may contain authentication data that indicates to the control module 404 that the instrument 100 is a valid device. One example is to set the UID to a value that corresponds to a valid UID in the database stored on the control module 404. Another example is to set the encrypted identifier such that the control module 404 may authenticate the instrument 100. More specifically, if the instrument 100 had previously been used by an operator, the authentication data may be replaced with the authentication data of an unused instrument 100.

Certain aspects of the invention may be disclosed in the following exemplary clauses.

Clause 1: A surgical instrument configured to be operated by a generator for removal of uterine fibroids, the surgical instrument comprising: a handpiece having opposed shells secured together with a fastener, a shroud secured to the handpiece and overlaying the fastener and a portion of the handpiece; an outer shaft extending from the shroud and defining a cutting window; a cutting shaft movable within the outer shaft and including a cutting tip for resecting the uterine fibroids within the cutting window; and a memory module configured to store instrument management data, and further configured to be arranged in electronic communication with the generator so as to communicate the instrument management data the generator for enabling or disabling of the surgical instrument.

Clause 2: The surgical instrument of clause 1, wherein the instrument management data comprises use data being at least one of (i) a number of times the surgical instrument has been used, (ii) the amount of time that the surgical instrument has been used, and (iii) a time stamp indicating when the surgical instrument was created.

Clause 3: The surgical instrument of any one of clause 1 and 2, wherein the instrument management data comprises and authentication data being a unique identifier or an encrypted identifier.

Clause 4: The surgical instrument of any one of clauses 1-3, wherein the memory module is a radiofrequency identification tag.

Clause 5: The surgical instrument of clause 4, wherein the RFID tag is coupled to the handpiece.

Clause 6: The surgical instrument of clause 5, wherein the RFID tag is coupled to the outer shaft.

Clause 7: The surgical instrument of any one of clauses 1-3, wherein the memory module is electrically erasable read-only memory (EEPROM).

Clause 8: A method of reprocessing the surgical instrument of any one of clauses 1-7, the method comprising: mutilating the shroud so as to remove the shroud from the handpiece; removing the memory module; securing a replacement memory module to the surgical instrument; and securing a replacement shroud to the handpiece.

Clause 9: A method of reprocessing the surgical instrument of any one of clauses 1-8, the method comprising replacing the instrument management data stored on the memory module.

Clause 10: The method of clause 9, wherein the step of replacing the instrument management data further comprises overwriting and erasing and rewriting the instrument management data to identify the surgical instrument as being permitted for reuse.

Clause 11: The method of clause 10, wherein the instrument management data comprises at least one of use data and authentication data, wherein the use data comprises at least one of a number of times the surgical instrument has been used, the amount of time that the surgical instrument has been used, and a time stamp indicating when the surgical instrument was created, and wherein the authentication data comprising at least one of a unique identifier and an encrypted identifier.

Clause 12: A method of reprocessing a surgical instrument after use for resecting tissue, wherein the surgical instrument includes a memory module storing a unique identifier and instrument management data including at least one of a usage value and a total use time value, the method comprising: authenticating the surgical instrument by using a password or key; reading the instrument management data stored in the memory module; comparing the instrument management data with previous instrument management data prior to the use that stored on a database and associated with the unique identifier; updating the instrument management data to provide updated instrument management data; storing the updated instrument management data on the database; and writing or resetting the updated instrument management data to the memory module to permit subsequent use of the surgical instrument with authentication of the unique identifier and the instrument management data.

Clause 13: The method of clause 12, wherein the step of authenticating the surgical instrument further comprises verifying at least one of (i) the unique identifier is not on a list of prohibited UIDs, (ii) the usage value does not exceed a usage limitation value, and (iii) the total use time value does not exceed a total use time limitation value.

Clause 14: The method of clause 13, wherein the database stores a list of valid unique identifiers and/or a list of prohibited unique identifiers, the method further comprising: receiving the unique identifier from the memory module; comparing the unique identifier against the lists of valid unique identifiers and/or the list of prohibited unique identifiers; and at least one of (i) permit subsequent use of the surgical instrument if the unique identifier is on the list of valid unique identifiers, and (ii) prohibit subsequent use of the surgical instrument if the unique identifier is on the list of prohibited unique identifiers.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations and embodiments have been discussed in the foregoing description. However, the configurations and embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

The invention claimed is:

1. A method of reprocessing a surgical instrument including a handpiece having opposed shells secured together with a fastener, a shroud secured to the handpiece and overlaying the fastener and a portion of the handpiece, an outer shaft extending from the shroud and defining a cutting window, and a cutting shaft movable within the outer shaft and including a cutting tip for resecting tissue within the cutting window, said method comprising:
   securing the surgical instrument to a fixture;
   removing the shroud from the handpiece by a process which includes milling the shroud;
   removing the fastener;

separating the opposed shells to access an interior of the handpiece;

servicing or replacing at least one component within the interior of the handpiece;

securing the opposed shells to one another with the fastener or another fastener; and securing a replacement shroud to the handpiece.

2. The method of claim 1, further comprising:

severing at least the cutting tip from the cutting shaft; and securing a replacement cutting tip to the cutting shaft.

3. The method of claim 1, further comprising:

removing the cutting shaft from the outer shaft; and sharpening the cutting tip of the cutting shaft.

4. The method of claim 1, further comprising chemically or electrically treating at least one of the outer shaft and the cutting shaft.

5. The method of claim 1, wherein the step of servicing or replacing at least one component further comprises replacing a suction tubing assembly with a replacement suction tubing assembly.

6. The method of claim 1, wherein the step of servicing or replacing at least one component further comprises:

decoupling a suction tubing assembly from the handpiece;

flushing the suction tubing assembly; and recoupling the suction tubing assembly to the handpiece.

7. The method of claim 1, wherein the surgical instrument further includes a flexible drive cable, and wherein the step of servicing or replacing at least one component further comprises (i) decoupling, cleaning, and recoupling the flexible drive cable, or (ii) replacing the flexible drive cable with a replacement flexible drive cable.

8. The method of claim 1, further comprising straightening at least one of the outer shaft and the cutting shaft.

9. The method of claim 1, further comprising:

milling the portion of the handpiece to provide a milled surface; and securing the replacement shroud to the milled surface.

10. The method of claim 9, further comprising applying an adhesive to the milled surface to secure the replacement shroud to the handpiece.

11. The method of claim 1, wherein the surgical instrument further includes original indicia disposed on the outer shaft, said method further comprising marking the outer shaft with updated indicia.

12. The method of claim 11, wherein the updated indicia is at least partially disposed over the original indicia.

13. The method of claim 11, wherein the updated indicia offset from the original indicia by a distance no greater than a predetermined threshold.

14. A method of reprocessing a surgical instrument including a handpiece having opposed shells, and a shroud secured to the handpiece and overlaying a portion of each of the opposed shells, said method comprising:

securing the surgical instrument to a fixture;

milling the shroud so as to remove the shroud from the portions of the opposed shells;

milling the portion of the opposed shells to provide a milled surface;

servicing or replacing at least one component within an interior of the handpiece; and securing a replacement shroud to the milled surface, wherein the shroud is formed from a first material and the replacement shroud is formed from a second material different than the first material.

15. The method of claim 14, wherein the second material is a bio-based polymer that is more environmentally sustainable than the first material.

16. The method of claim 14, further comprising applying an adhesive to the milled surface to secure the replacement shroud to the handpiece.

17. A method of replacing a shroud of a surgical instrument, the instrument including a handpiece having opposing shells and the shroud overlaying a portion of each of the opposed shells, said method comprising:

securing the surgical instrument to a fixture;

milling the shroud so as to remove the shroud from the portions of the opposed shells;

milling the portion of the opposed shells to provide a milled surface; and securing a replacement shroud to the milled surface, wherein the shroud is formed from a first material and the replacement shroud is formed from a second material different than the first material.

* * * * *